(12) United States Patent
Heuer et al.

(10) Patent No.: US 7,906,154 B2
(45) Date of Patent: *Mar. 15, 2011

(54) COMPOSITIONS AND METHODS FOR THE INDUCTION AND MAINTENANCE OF QUALITY SLEEP

(76) Inventors: Marvin A. Heuer, Mississauga (CA); Shan Chaudhuri, Mississauga (CA); Kenneth Clement, Mississauga (CA)

( * ) Notice: Subject to any disclaimer, the term of this patent is extended or adjusted under 35 U.S.C. 154(b) by 771 days.

This patent is subject to a terminal disclaimer.

(21) Appl. No.: 11/821,229

(22) Filed: Jun. 21, 2007

(65) Prior Publication Data

US 2007/0264337 A1 Nov. 15, 2007

Related U.S. Application Data

(62) Division of application No. 11/486,866, filed on Jul. 14, 2006, now Pat. No. 7,476,405.

(60) Provisional application No. 60/776,325, filed on Feb. 23, 2006.

(51) Int. Cl.
| | |
|---|---|
| *A61K 36/84* | (2006.01) |
| *A61K 36/76* | (2006.01) |
| *A61K 31/4045* | (2006.01) |
| *A61K 36/53* | (2006.01) |
| *A61K 36/539* | (2006.01) |
| *A61K 36/00* | (2006.01) |
| *A61K 9/22* | (2006.01) |
| *A61K 9/28* | (2006.01) |
| *A61K 9/14* | (2006.01) |

(52) U.S. Cl. ......... 424/725; 424/773; 424/775; 424/778; 424/468; 424/474; 424/489; 514/923

(58) Field of Classification Search ........................ None
See application file for complete search history.

(56) References Cited

U.S. PATENT DOCUMENTS

| | | |
|---|---|---|
| 5,641,801 A | 6/1997 | Wurtman |
| 5,681,578 A | 10/1997 | Sahley |
| 5,716,978 A | 2/1998 | Lewy |
| 6,080,410 A | 6/2000 | Bewicke |
| 6,277,396 B1 | 8/2001 | Dente |
| 6,312,736 B1 | 11/2001 | Kelly et al. |
| 6,383,527 B1 | 5/2002 | Artman et al. |
| 6,579,543 B1 | 6/2003 | McClung |
| 6,703,412 B1 | 3/2004 | Rosenthal |
| 6,770,263 B1 | 8/2004 | Brucker |
| 6,869,622 B2 | 3/2005 | Andrews et al. |
| 7,045,158 B2 | 5/2006 | Wolfson et al. |
| 2001/0011083 A1* | 8/2001 | Barr et al. ............... 514/159 |
| 2002/0127285 A1* | 9/2002 | Xiu ......................... 424/725 |
| 2003/0013639 A1 | 1/2003 | Yurchak et al. |
| 2003/0232091 A1 | 12/2003 | Shefer et al. |
| 2004/0063661 A1* | 4/2004 | Linnane .................... 514/50 |
| 2004/0247699 A1 | 12/2004 | Delsing |
| 2005/0129783 A1 | 6/2005 | McClearly et al. |
| 2005/0244517 A1 | 11/2005 | Hall et al. |
| 2005/0272690 A1* | 12/2005 | Cremisi ..................... 514/52 |

FOREIGN PATENT DOCUMENTS

| | | |
|---|---|---|
| HU | 62477 | 5/1993 |
| HU | 62477 T * | 5/1993 |
| WO | 2005/097101 | 10/2005 |

OTHER PUBLICATIONS

Widy-tyszikiewicz et al, a randomized double blind study of sedative effects of phytotherapeutic containing valerian, hops, balm and motherworth versus placebo, Herba polonica, Tom XLIII 1997, No. 2, pp. 154-159.*
Farmer et al: "Potential effects of herbal medicinals on perioperative care" Seminars in Anesthesia, Saunders, CO, New York, NY, US, vol. 20, No. 2, Jun. 1, 2001, pp. 110-117.
Supplementary European Search Report for EP 06 76 1118.
Horne, et al., "Aspirin and Human Sleep", Electrenceph. and Clin. Neurophys., vol. 49 (1980) 409-13.
Murphy, et al., "Nonsteroidal Anti-Inflammatory Drugs Affect Normal Sleep Patterns in Humans", Phys. and Behavior, vol. 55, No. 6 (1994) 1063-66.
Valenstein et al., "Benzodiazepine use among depressed patients treated in mental health settings", Am J Psychiatry, vol. 161, No. 4 (2004) 654-61.
Ringdahl, et al., "Treatment of Primary Insomnia", JABFP, vol. 17, No. 3 (2004) 212-19.
Benca et al., "Diagnosis and Treatment of Chronic Insomnia", Psych. Serv., vol. 56, No. 3 (2005) 332-43.
Abourashed EA, Koetter U, Brattstrom A. In vitro binding experiments with a Valerian, hops and their fixed combination extract (Ze91019) to selected central nervous system receptors. Phytomedicine. Nov. 2004;11(7-8):633-8.).
Akhondzadeh et al, Melissa officinalis extract in the treatment of patients with mild to moderate Alzheimer's disease: a double blind, randomised, placebo controlled trial. J Neurol Neurosurg Psychiatry. Jul. 2003;74(7):863-6.
Akhondzadeh et al., Comparison of Lavandula angustifolia Mill. tincture and imipramine in the treatment of mild to moderate depression: a double-blind, randomized trial. Prog Neuropsychopharmacol Biol Psychiatry. Feb. 2003;27(1):123-7.

(Continued)

Primary Examiner — Qiuwen Mi

(57) ABSTRACT

Supplemental compositions, and methods for administering same to a user, are provided for promoting a restful night's sleep by speedily inducing a person to fall asleep and to maintain sleep, as well as alleviating minor aches and pains so as to further improve the quality of a person sleep. The supplemental composition may include at least an extract of Valerian Root, an extract of Willow Bark and Melatonin or a derivative thereof. The supplemental composition may be provided for consumption at least one time daily, e.g., prior to sleep.

8 Claims, No Drawings

OTHER PUBLICATIONS

Akhondzadeh et al., Passionflower in the treatment of generalized anxiety: a pilot double-blind randomized controlled trial with oxazepam. J Clin Pharm Ther. Oct. 2001;26(5):363-7.

Andrade R. of membrane excitability in the central nervous system by serotonin receptor subtypes. Ann N Y Acad Sci. Dec. 15, 1998;861:190-203.

Aoshima et al., Effects of beer and hop on ionotropic gamma-aminobutyric acid receptors. J Agric Food Chem. Apr. 5, 2006;54(7):2514-9.).

Arangino et al., Effects of melatonin on vascular reactivity, catecholamine levels, and blood pressure in healthy men. Am J Cardiol. May 1, 1999;83(9):1417-9.

Avery et al., Guidelines for prescribing melatonin. Ann Med. Feb. 1998;30(1):122-30.

Awad et al., Phytochemical and biological analysis of skullcap (*Scutellaria lateriflora L.*): a medicinal plant with anxiolytic properties. Phytomedicine. Nov. 2003;10(8):640-9.

Brzezinski et al., Effects of exogenous melatonin on sleep: a meta-analysis. Sleep Med Rev. Feb. 2005;9(1):41-50.

Buscemi et al., The efficacy and safety of exogenous melatonin for primary sleep disorders. A meta-analysis. J Gen Intern Med. Dec. 2005;20(12):1151-8.

Chrubasik et al., Treatment of low back pain exacerbations with willow bark extract: a randomized double-blind study. Am J Med. Jul. 2000;109(1):9-14.

Dietz et al., Valerian extract and valerenic acid are partial agonists of the 5-HT5a receptor in vitro. Brain Res Mol Brain Res. Aug. 18, 2005;138(2):191-7.

Dietz et al., Xanthohumol isolated from Humulus lupulus Inhibits menadione-induced DNA damage through induction of quinone reductase. Chem Res Toxicol. Aug. 2005;18(8):1296-305.

Dijk et al., Integration of human sleep-wake regulation and circadian rhythmicity. J Appl Physiol. Feb. 2002;92(2):852-62.

Dimpfel et al,. Effects of lozenge containing lavender oil, extracts from hops, lemon balm and oat on electrical brain activity of volunteers. Eur J Med Res. Sep. 29, 2004;9(9):423-31.

Dubocovich et al., Functional MT1 and MT2 melatonin receptors in mammals. Endocrine. Jul. 2005;27(2)101-10.

Everson CA. Sustained sleep deprivation impairs host defense. Am J Physiol. Nov. 1993;265(5 Pt 2):R1148-54.

Feng et al.. Serotonin receptors modulate GABA(A) receptor channels through activation of anchored protein kinase C in prefrontal cortical neurons. J Neurosci. Sep. 1, 2001;21(17):6502-11.

Francis et al., Effect of valerian, *Valeriana edulis*, on sleep difficulties in children with intellectual deficits: randomised trial. Phytomedicine. May 2002;9(4):273-9.

Fussel et al., Effect of a fixed valerian-Hop extract combination (Ze 91019) on sleep polygraphy in patients with non-organic insomnia: a pilot study. Eur J Med Res. Sep. 18, 2000;5(9):385-90.

Gafner et al., Inhibition of [3H]-LSD binding to 5-HT7 receptors by flavonoids from Scutellaria lateriflora. J Nat Prod. Apr. 2003;66(4):535-7.

Gais et al., Early sleep triggers memory for early visual discrimination skills. Nat Neurosci. Dec. 2000;3(12):1335-9.

Gottlieb et al., Association of sleep time with diabetes mellitus and impaired glucose tolerance. Arch Intern Med. Apr. 25, 2005;165(8):863-7.

Gyllenhaal et al., Efficacy and safety of herbal stimulants and sedatives in sleep disorders. Sleep Med Rev. Jun. 2000;4(3):229-251.

Hastings MH. Central clocking. Trends Neurosci. Oct. 1997;20(10):459-64.

Hohmann et al., Protective effects of the aerial parts of *Salvia officinalis, Melissa officinalis* and *Lavandula angustifolia* and their constituents against enzyme-dependent and enzyme-independent lipid peroxidation. Planta Med. Aug. 1999;65(6):576-8.

Holmes et al., Lavender oil as a treatment for agitated behaviour in severe dementia: a placebo controlled study. Int J Geriatr Psychiatry. Apr. 2002;17(4):305-8.

Hughes et al., The role of melatonin and circadian phase in age-related sleep-maintenance insomnia: assessment in a clinical trial of melatonin replacement. Sleep. 1998;21(1):52-68.

Imagawa et al.,Coenzyme Q10, iron, and vitamin B6 in genetically-confirmed Alzheimer's disease. Lancet. Sep. 12, 1992;340(8820):671.

Irwin et al., Partial night sleep deprivation reduces natural killer and cellular immune responses in humans. FASEB J. Apr. 1996;10(5):643-53.

Kamikawa et al., Effects of coenzyme Q10 on exercise tolerance in chronic stable angina pectoris. Am J Cardiol. Aug. 1, 1985;56(4):247-51.

Kayumov et al., A randomized, double-blind, placebo-controlled crossover study of the effect of exogenous melatonin on delayed sleep phase syndrome. Psychosom Med. Jan.-Feb. 2001;63(1):40-8.

Kennedy et al. Modulation of mood and cognitive performance following acute administration of *Melissa officinalis* (lemon balm). Pharmacol Biochem Behav. Jul. 2002;72(4):953-64.

Kennedy et al., Anxiolytic effects of a combination of *Melissa officinalis* and *Valeriana officinalis* during laboratory induced stress. Phytother Res. Feb. 2006;20(2):96-102.

Kennedy et al., Modulation of mood and cognitive performance following acute administration of single doses of *Melissa officinalis* (Lemon balm) with human CNS nicotinic and muscarinic receptor-binding properties. Neuropsychopharmacology. Oct. 2003;28(10):1871-81.

Kennedy et al.,. Attenuation of laboratory-induced stress in humans after acute administration of *Melissa officinalis* (Lemon Balm). Psychosom Med. Jul.-Aug. 2004;66(4):607-13.

Kunz et al., Melatonin in patients with reduced REM sleep duration: two randomized controlled trials. J Clin Endocrinol Metab. Jan. 2004;89(1):128-34.

Langsjoen et al., Treatment of essential hypertension with coenzyme Q10. Mol Aspects Med. 1994;15 Suppl:S265-72.

Leathwood et al., Aqueous extract of valerian root (*Valeriana officinalis L.*) improves sleep quality in man. Pharmacol Biochem Behav. Jul. 1982;17(1):65-71.

Lindahl et al., Double blind study of a valerian preparation. Pharmacol Biochem Behav. Apr. 1989;32(4):1065-6.

Lis-Balchin et al., Studies on the mode of action of the essential oil of lavender (*Lavandula angustifolia* P. Miller). Phytother Res. Sep. 1999;13(6):540-2.

Matsumoto M. The hypnotic effects of melatonin treatment on diurnal sleep in humans. Psychiatry Clin Neurosci. Apr. 1999;53(2):243-5.

Mendelson WB. Sleep-inducing effects of adenosine microinjections into the medial preoptic area are blocked by flumazenil. Brain Res. Jan. 10, 2000;852(2):479-81.

Menghini et al, TLC determination of flavonoid accumulation in clonal populations of Passiflora incarnata L. Pharmacol Res Commun. Dec. 1988;20 Suppl 5:113-6.

Mortensen SA. Perspectives on therapy of cardiovascular diseases with coenzyme Q10 (ubiquinone). Clin Investig. 1993;71(8 Suppl):S116-23.

Muller CE, Schumacher B, Brattstrom A, Abourashed EA, Koetter U. Interactions of valerian extracts and a fixed valerian-hop extract combination with adenosine receptors. Life Sci. Sep. 6, 2002;71(16):1939-49.

Mundey et al., Phase-dependent treatment of delayed sleep phase syndrome with melatonin. Sleep. Oct. 1, 2005;28(10):1271-8.

Nagtegaal et al., Delayed sleep phase syndrome: A placebo-controlled cross-over study on the effects of melatonin administered five hours before the individual dim light melatonin onset. J Sleep Res. Jun. 1998;7(2):135-43.

Ninomiya et al., Effects of exogenous melatonin on pituitary hormones in humans. Clin Physiol. May 2001;21(3):292-9.

Olsen et al., Molecular biology of GABAA receptors. FASEB J. 19 Valenstein M, Taylor KK, Austin K, Kales HC, McCarthy JF, Blow FC. Benzodiazepine use among depressed patients treated in mental health settings. Am J Psychiatry. Apr. 2004;161(4):654-61.).90 Mar;4(5):1469-80).

Pereira et al., A HPTLC densitometric determination of flavonoids from *Passiflora alata, P. edulis, P. incarnata* and *P. caerulea* and comparison with HPLC method. Phytochem Anal. Jul.-Aug. 2004;15(4):241-8.

Portas et al., On-line detection of extracellular levels of serotonin in dorsal raphe nucleus and frontal cortex over the sleep/wake cycle in the freely moving rat. Neuroscience. Apr. 1998;83(3):807-1.

Reiter RJ. melatonin: cell biology of its synthesis and of its physiological interactions. Endocr Rev. May 1991;12(2):151-80.

Roth et al., Daytime consequences and correlates of insomnia in the United States: results of the 1991 National Sleep Foundation Survey. II. Sleep. May 1, 1999;22 Suppl 2:S354-8.

Sandor et al., J. Efficacy of coenzyme Q10 in migraine prophylaxis: a randomized controlled trial. Neurology. Feb. 22, 2005;64(4):713-5.

Sawynok J. Pharmacological rationale for the clinical use of caffeine. Drugs. Jan. 1995;49(1):37-50.

Schmid et al., Efficacy and tolerability of a standardized willow bark extract in patients with osteoarthritis: randomized placebo-controlled, double blind clinical trial. Phytother Res. Jun. 2001;15(4):344-50.

Shults et al., Coenzyme Q10 levels correlate with the activities of complexes I and II/III in mitochondria from parkinsonian and nonparkinsonian subjects. Ann Neurol. Aug. 1997;42(2):261-4.

Shults et al., Parkinson Study Group. Effects of coenzyme Q10 in early Parkinson disease: evidence of slowing of the functional decline. Arch Neurol. Oct. 2002;59(10):1541-50.

Soja AM, Mortensen SA. Treatment of congestive heart failure with coenzyme Q10 illuminated by meta-analyses of clinical trials. Mol Aspects Med. 1997;18 Suppl:S159-68.

Soulimani et al., Behavioural effects of *Passiflora incarnata L.* and its indole alkaloid and flavonoid derivatives and maltol in the mouse. J Ethnopharmacol. Jun. 1997;57(1):11-20.

Stickgold et al., Visual discrimination learning requires sleep after training. Nat Neurosci. Dec. 2000;3(12):1237-8.

Stoller MK. Economic effects of insomnia. Clin Ther. Sep.-Oct. 1994;16(5):873-97.

Strecker et al., Adenosinergic modulation of basal forebrain and preoptic/anterior hypothalamic neuronal activity in the control of behavioral state. Behav Brain Res. Nov. 2000;115(2):183-204.

Takasaki et al., An Analysis of Effectiveness of Activated Co-enzyme Q10 on Subjects by Using Acoustic Technology. Biopharma Ltd. Tokyo Japan, 2006.

Thakkar et al., A1 receptor and adenosinergic homeostatic regulation of sleep-wakefulness: effects of antisense to the A1 receptor in the cholinergic basal forebrain. J Neurosci. May 15, 2003;23(10):4278-87.

Thomas et al., Inhibition of LDL oxidation by ubiquinol-10. A protective mechanism for coenzyme Q in atherogenesis? Mol Aspects Med. 1997;18 Suppl:S85-103.

Valenstein et al., Benzodiazepine use among depressed patients treated in mental health settings. Am J Psychiatry. Apr. 2004;161(4):654-61.

Wake et al., E. acetylcholine receptor activity in European medicinal plants traditionally used to improve failing memory. J Ethnopharmacol. Feb. 2000;69(2):105-14.

Weber et al., Antioxidative effect of dietary coenzyme Q10 in human blood plasma.. Int J Vitam Nutr Res. 1994;64(4):311-5.

Wolfman et al., Possible anxiolytic effects of chrysin, a central benzodiazepine receptor ligand isolated from *Passiflora coerulea*. Pharmacol Biochem Behav. Jan. 1994;47(1):1-4.

Wolfson et al., An investigation into the efficacy of Scutellaria lateriflora in healthy volunteers. Altern Ther Health Med. Mar.-Apr. 2003;9(2):74-8.

Wyatt et al., . Circadian temperature and melatonin rhythms, sleep, and neurobehavioral function in humans living on a 20-h day. Am J Physiol. Oct. 1999;277(4 Pt 2):R1152-63.

Zammit et al., Quality of life in people with insomnia. Sleep. May 1, 1999;22 Suppl 2:S379-85.

Zanoli P, Rivasi M, Zavatti M, Brusiani F, Baraldi M. New insight in the neuropharmacological activity of *Humulus lupulus L.* J Ethnopharmacol. Oct. 31, 2005;102(1):102-6.

Zeitzer et al., Extracellular adenosine in the human brain during sleep and sleep deprivation: an in vivo microdialysis study. Sleep. Apr. 1, 2006;29(4):455-61.

Zhdanova et al., Melatonin treatment for age-related insomnia. J Clin Endocrinol Metab. Oct. 2001;86(10):4727-30.

Zhdanova et al., Sleep-inducing effects of low doses of melatonin ingested in the evening. Clin Pharmacol Ther. May 1995;57(5):552-8.

* cited by examiner

COMPOSITIONS AND METHODS FOR THE INDUCTION AND MAINTENANCE OF QUALITY SLEEP

CROSS-REFERENCE TO RELATED APPLICATIONS

This application is a divisional and claims the benefit of priority of U.S. patent application Ser. No. 11/486,866 (U.S. Pat. No. 7,476,405) filed Jul. 14, 2006, which is hereby incorporated by reference in its entirety, which in turn is related to and claims the benefit of priority to the Applicant's U.S. Provisional Patent Application Ser. No. 60/776,325, filed Feb. 23, 2006, now the Applicant's U.S. patent application Ser. Nos. 11/709,525 now abandoned and 11/709,526 entitled "Method For Increasing The Rate And Consistency Of Bioavailability Of Supplemental Dietary Ingredients" and "Method for a Supplemental Dietary Composition Having a Multi-Phase Dissolution Profile" respectively, filed Feb. 21, 2007, the disclosures of which are hereby fully incorporated by reference.

FIELD OF THE INVENTION

The present invention relates to a composition to aid in the induction and maintenance of sleep in a user, e.g., human.

BACKGROUND OF THE INVENTION

Sleep typically occupies about one-third of a person's life and affects a person's mental and physical well-being. It additionally affects mood, behavior and physiology. Sleep and the control of sleep is a complex process involving multiple chemicals and brain structures. It is a dynamic process involving distinct physiological changes and involves both positive and negative signaling. The regulation of sleep in humans is governed by three processes—each influenced by hormonal and environmental factors: a daily sleep-wake cycle influenced by a circadian rhythm (24 hour cycle) tied to light-dark cycles controlled by a cluster of about 10,000 neurons located in the hypothalamus behind the eyes, called the suprachiasmatic nuclei (Hastings M H. Central clocking. Trends Neurosci. October 1997; 20(10):459-64); a separable oscillating sleep homeostatic process influenced by prior sleep (Dijk D J, Lockley S W. Integration of human sleep-wake regulation and circadian rhythmicity. J Appl Physiol. February 2002; 92(2):852-62); and an ultradian rhythm which occurs within the 24 hour circadian cycle.

The need for sleep is a biological drive similar to thirst or hunger. Interestingly though, the function of sleep is largely unknown, however some evidence indicates that sleep is required for learning (Stickgold R, James L, Hobson J A. Visual discrimination learning requires sleep after training. Nat Neurosci. December 2000; 3(12):1237-8; Gais S, Plihal W, Wagner U, Born J. Early sleep triggers memory for early visual discrimination skills. Nat Neurosci. December 2000; 3(12):1335-9). Additionally, sleep deprivation studies in rats have shown that when rats are not allowed to sleep, the end-result is death apparently related to immune system failure (Everson C A. Sustained sleep deprivation impairs host defense. Am J Physiol. November 1993; 265(5 Pt 2):R1148-54). In humans, similarly, mild sleep deprivation also results in indications of impaired immune system function (Irwin M, McClintick J, Costlow C, Fortner M, White J, Gillin J C. Partial night sleep deprivation reduces natural killer and cellular immune responses in humans. FASEB J. April 1996; 10(5):643-53). Although specific sleep requirements vary from individual to individual, sleeping less than six hours per day has been shown to increase the risk of glucose intolerance and diabetes (Gottlieb D J, Punjabi N M, Newman A B, Resnick H E, Redline S, Baldwin C M, Nieto F J. Association of sleep time with diabetes mellitus and impaired glucose tolerance. Arch Intern Med. Apr. 25, 2005; 165(8):863-7). Insomnia has been estimated to affect 40% of North Americans per year (Stoller M K. Economic effects of insomnia. Clin Ther. September-October 1994; 16(5):873-97). A study by the U.S. National Sleep Foundation and the Gallup Organization involving 1,000 randomly selected Americans revealed that insomnia negatively impacts activities during waking function and effects quality of life (Roth T, Ancoli-Israel S. Daytime consequences and correlates of insomnia in the United States: results of the 1991 National Sleep Foundation Survey. II. Sleep. May 1, 1999; 22 Suppl 2:S354-8). Another study involving 261 insomnia sufferers and 101 individuals with no sleep complaints revealed that insomnia significantly impairs quality of life (Zammit G K, Weiner J, Damato N, Sillup G P, McMillan C A. Quality of life in people with insomnia. Sleep. May 1, 1999; 22 Suppl 2:S379-85).

The neurotransmitter Gamma Aminobutyric Acid (GABA) is a primary inhibitory neurotransmitter. One of its effects is to induce sleep. The GABA-receptors are associated with chloride ion channels—signaling through the GABA-receptor changes the electrochemical gradient of the neuron, leading to activity inhibition (Olsen R W, Tobin A J. Molecular biology of GABAA receptors. FASEB J. March 1990; 4(5):1469-80). Benzodiazepines are thought to act via interaction with the GABA receptor; enhancing the inhibitory effects of GABA. As such, Benzodiazepines are a widely used class of drugs primarily used as tranquilizers, muscle-relaxants, hypnotics or sedatives (Valenstein M, Taylor K K, Austin K, Kales H C, McCarthy J F, Blow F C. Benzodiazepine use among depressed patients treated in mental health settings. Am J Psychiatry. April 2004; 161(4):654-61). Additionally, Adenosine, a neuromodulator, may induce sleep by extracellular accumulation in specific brain regions such as the basal forebrain during prolonged wakefulness (Strecker R E, Morairty S, Thakkar M M, Porkka-Heiskanen T, Basheer R, Dauphin L J, Rainnie D G, Portas C M, Greene R W, McCarley R W. Adenosinergic modulation of basal forebrain and preoptic/anterior hypothalamic neuronal activity in the control of behavioral state. Behav Brain Res. November 2000; 115(2):183-204; Zeitzer J M, Morales-Villagran A, Maidment N T, Behnke E J, Ackerson L C, Lopez-Rodriguez F, Fried I, Engel J Jr, Wilson C L. Extracellular adenosine in the human brain during sleep and sleep deprivation: an in vivo microdialysis study. Sleep. Apr. 1, 2006; 29(4):455-61). Actions on both the GABA-benzodiazepine receptor complex (Mendelson W B. Sleep-inducing effects of adenosine microinjections into the medial preoptic area are blocked by flumazenil. Brain Res. Jan. 10, 2000; 852(2):479-81) and/or the adenosine A1 receptor (Thakkar M M, Winston S, McCarley R W. A1 receptor and adenosinergic homeostatic regulation of sleep-wakefulness: effects of antisense to the A1 receptor in the cholinergic basal forebrain. J Neurosci. May 15, 2003; 23(10):4278-87) can lead to the induction and maintenance of sleep. The stimulatory effects of caffeine are thought to be due to antagonism of adenosine A1 receptors (Sawynok J. Pharmacological rationale for the clinical use of caffeine. Drugs. January 1995; 49(1):37-50), wherein an aroused state is observed.

Another chemical associated with sleep is Melatonin. It is a hormone produced by the pineal gland from the amino acid tryptophan. Production is rhythmic in keeping with an intrinsic cycle of approximately 24-hours in duration, wherein levels are low during the day and increasing towards the nighttime (Wyatt J K, Ritz-De Cecco A, Czeisler C A, Dijk D J. Circadian temperature and melatonin rhythms, sleep, and neurobehavioral function in humans living on a 20-h day. Am J Physiol. October 1999; 277(4 Pt 2):R1152-63). Melatonin appears to have two distinct effects on the circadian clock: neuronal inhibition and phase-shifting of the sleep cycle (Liu C, Weaver D R, Jin X, Shearman L P, Pieschl R L, Gribkoff V K, Reppert S M. Molecular dissection of two distinct actions of melatonin on the suprachiasmatic circadian clock. Neuron. July 1997; 19(1):91-102). Oral administration of supplemental melatonin during the day induces sleepiness and improves night sleep (Dollins A B, Zhdanova I V, Wurtman R J, Lynch H J, Deng M H. Effect of inducing nocturnal serum melatonin concentrations in daytime on sleep, mood, body temperature, and performance. Proc Natl Acad Sci USA. Mar. 1, 1994; 91(5):1824-8). Two types of melatonin G-protein coupled receptors have been classified in mammals and termed MT1 and MT2 (Dubocovich M L, Markowska M. Functional MT1 and MT2 melatonin receptors in mammals. Endocrine. July 2005; 27(2):101-10).

Serotonin (5-hydroxytryptamine, 5HT), like melatonin, also displays a diurnal pattern; however, it functions in an opposing rhythm with daytime levels being higher than nighttime levels Portas C M, Bjorvatn B, Fagerland S, Gronli J, Mundal V, Sorensen E, Ursin R. On-line detection of extracellular levels of serotonin in dorsal raphe nucleus and frontal cortex over the sleep/wake cycle in the freely moving rat. Neuroscience. April 1998; 83(3):807-1). Three basic serotonin receptor types have been identified: 5HT-1, 5HT-2 and 5HT-3. Several subtypes of 5HT-1 have also been identified. The exact response of cells to serotonin depends on the receptor types expressed (Andrade R. of membrane excitability in the central nervous system by serotonin receptor subtypes. Ann N Y Acad Sci. Dec. 15, 1998; 861:190-203) however, Serotonin has been shown to inhibit GABA receptors (Feng J, Cai X, Zhao J, Yan Z. Serotonin receptors modulate GABA (A) receptor channels through activation of anchored protein kinase C in prefrontal cortical neurons. J Neurosci. Sep. 1, 2001; 21(17):6502-11), likely contributing to the opposing actions of serotonin and GABA and play a role in sleep.

SUMMARY OF THE INVENTION

The present invention according to one embodiment thereof, provides for a composition directed towards the induction of sleep. More specifically, the invention is directed towards a sleep-promoting and pain-relief composition. Advantageously, the sleep-promoting and pain-relief composition of the present invention may additionally provide for maintenance of sleep, thereby promoting a good quality, restful sleep as well as alleviating minor aches and pains, thus further improving the quality of the person's sleep. The composition of the present invention comprises an extract of Valerian Root, an extract of Willow Bark and Melatonin or a derivative thereof. For example, the present invention may be effective in promoting a restful night's sleep by speedily inducing a person to fall asleep and maintain sleep as well as alleviating minor aches and pains further improving the quality of an individual's, e.g. a human or animal, sleep. Furthermore, the present invention advantageously provides a method for the maintenance of sleep thereby promoting a good quality, restful sleep as well as alleviating minor aches and pains, thus further improving the quality of an individual's, e.g. human or animal, sleep by administering to a human or a animal a composition comprising an extract of Valerian Root, an extract of Willow Bark and Melatonin or a derivative thereof.

According to an embodiment, the present invention may provide a composition comprising an extract of Valerian Root, an extract of Willow Bark and Melatonin or a derivative thereof. Additionally, the composition may include one or more of an extract of Hops cone, Lavender flower powder, an extract of Passionflower, Skullcap powder, an extract of Coenzyme Q10, a leaf of extract Lemon Balm. The composition may include a time-release mechanism, e.g., wherein the time-release mechanism provides 4 hours of active compound release. Also, the melatonin may be incorporated into a tablet coating to promote sleep more quickly, e.g., to promote instant or immediate sleep. Also, in an embodiment of the present invention, all or a portion of the melatonin may be fine-milled. Advantageously, the extract of Valerian Root, the extract of Willow Bark and the Melatonin or a derivative thereof, are provided in amounts effective to at least one of promote sleep and relieve pain.

DETAILED DESCRIPTION OF THE INVENTION

The present invention according to an embodiment thereof is advantageously directed towards a sleep-promoting and pain-relief composition which, for example, may induce sleep and promote the maintenance of sleep leading to a restful night's sleep, as well as alleviate minor aches and pains, further improving the quality of a person's sleep. Compounds employed in various embodiments of the present invention have been shown to be active at receptor sites in the central nervous system that relate to the induction and maintenance of sleep. Moreover, the composition of the present invention also contains compounds shown to alleviate minor aches and pains.

In an embodiment, the present invention may include the use of combinations, wherein the combination includes, without being limited to, one or more of the following: Melatonin, Coenzyme Q10, Lemon Balm leaf extract, Hops cone extract, Lavender flower extract, Passionflower extract, Skullcap, deodorized Valerian root and Willow bark extract. The supplement may be consumed in any form, e.g., a capsule, a tablet, a caplet, a liquid beverage, a powder beverage mix, or as a dietary gel. The preferred dosage form of the present embodiment is a timed release caplet.

As set forth above, the dosage form of the diet supplement, in accordance with the example embodiment set forth below, may be provided in accordance with customary processing techniques for herbal and/or dietary supplements, wherein the active ingredients are suitably processed into a desired form. In accordance with an embodiment of the present invention, one or more ingredients of the diet supplement are processed so as to form fine-milled particles. For instance, in an embodiment, one or more ingredients of the supplemental dietary composition is processed by a large-scale dry milling technique that produces fine particles, preferably known as fine-milled particles. The use of dry milling techniques, in combination with excipients and polymers, to form fine-milled particles has been shown to improve flow and dispersability, stability, resistance to moisture, bioavailability, and dissolution/release properties. Formulations may benefit by containing fine-milled particles because providing one or more ingredients in fine-milled particle sizes may optimize one or more of the flow and dispersability, stability, resistance to moisture, bioavailability, and dissolution/release properties of the one or more ingredients in a diet supplement. In vitro tests designed to simulate the environment of a stomach were performed to test the dissolution rate of fine-milled particle tablets relative to tablets having particles that are not fine-milled. These test showed that in tablets produced from fine-milled particles the time to 100% dissolution was approximately 15 minutes. In the case of non-fine-milled particle compositions, only 90% dissolution was observed after 120 minutes. In a preferred embodiment, the supplemental composition contains fine-milled particles having an average size between about 2 nm and about 50 nm.

U.S. Provisional Patent Application 60/776,325 discloses a method for improving the absorption, palatability, taste, texture, and bioavailability of compounds by increasing the solubility of compounds in proprietary formulations for the purposes of enhancing or improving muscle size, growth and/or recovery time and/or weight loss. The increased bioavailability of the compound or ingredients is achieved by reducing the particle size via "fine-milling" thereby increasing the surface area-to-volume ratio of each particle, thus increasing the rate of dissolution. The compositions and methods disclosed promote increased bioavailability by increasing the total surface area of poorly soluble particles, thereby increasing the rate of absorption.

As used herein the, term "fine-milled" and/or "fine-milling" refers to the process of micronization. Micronization is a mechanical process that involves the application of force to a particle, thereby resulting in a reduction in the size of the particle. The force, in the case of micronization, may be applied in any manner such as, e.g., the collision of particles at high rates of speed, grinding, or by an air-jet micronizer. In a preferred embodiment, fine-milled particles are obtained by jet-milling with nitrogen and compressed air.

As used herein, the term "particle size" refers to the diameter of the particle. The term "average particle size" means that at least 50% of the particles in a sample will have the specified particle size. Preferably, at least 80% of the particles in a sample will have the specified particle size, and more preferably, at least 90% of the particles in a given sample will have the specified particle size.

The size of a particle can be determined by any of the methods known within the art. Methods for particle size determination which may be employed are, e.g., sieves, sedimentation, electrozone sensing (Coulter counter), microscopy, and/or Low Angle Laser Light Scattering. The preferred methods for the particle size determination of the present invention are the methods which are most commonly used in the pharmaceutical industry, such as laser diffraction, e.g., via light scattering Coulter Delsa 440SX.

The fine-milling process may be employed in the processing of one or more of the ingredients of the present invention in the dosage forms of tablets (e.g., immediate-release film coated, modified-release and fast-dissolving), capsules (e.g., immediate-release and modified-release), liquid dispersions, powders, drink mixes, etc.

Furthermore, the dosage form of the nutritional supplement in accordance with the aforementioned embodiment or further embodiments as interpreted by one of skill in the art related to the present invention may be provided in accordance with customary processing techniques for herbal and/or dietary and/or nutritional supplements in any of the forms mentioned above.

Melatonin

Melatonin is a hormone produced by the pineal gland from tryptophan and is involved in sleep regulation (Reiter R J. melatonin: cell biology of its synthesis and of its physiological interactions. Endocr Rev. May 1991; 12(2):151-80). It is used to treat sleep disorders such as insomnia and 'jet lag' by stimulating the release of specific pituitary hormones (Ninomiya T, Iwatani N, Tomoda A, Miike T. Effects of exogenous melatonin on pituitary hormones in humans. Clin Physiol. May 2001; 21(3):292-9) and adjusting the circadian rhythm to coincide with the local day and nighttime.

Melatonin supplementation has been demonstrated to be safe and effective at increasing the total amount of sleep time in healthy subjects (Matsumoto M. The hypnotic effects of melatonin treatment on diurnal sleep in humans. Psychiatry Clin Neurosci. April 1999; 53(2):243-5). Moreover, Melatonin has also been shown to benefit individuals suffering from insomnia (Hughes R J, Sack R L, Lewy A J. The role of melatonin and circadian phase in age-related sleep-maintenance insomnia: assessment in a clinical trial of melatonin replacement. Sleep. 1998; 21(1):52-68; Zhdanova I V, Wurtman R J, Regan M M, Taylor J A, Shi J P, Leclair O U. Melatonin treatment for age-related insomnia. J Clin Endocrinol Metab. October 2001; 86(10):4727-30; Brzezinski A, Vangel M G, Wurtman R J, Norrie G, Zhdanova I, Ben-Shushan A, Ford I. Effects of exogenous melatonin on sleep: a meta-analysis. Sleep Med Rev. February 2005; 9(1):41-50) by way of the induction of sleep. The most common effect of melatonin on sleep is a reduction in sleep latency, the time taken to fall asleep (Zhdanova I V, Wurtman R J, Lynch H J, Ives J R, Dollins A B, Morabito C, Matheson J K, Schomer D L. Sleep-inducing effects of low doses of melatonin ingested in the evening. Clin Pharmacol Ther. May 1995; 57(5):552-8; Nagtegaal J E, Kerkhof G A, Smits M G, Swart A C, Van Der Meer Y G. Delayed sleep phase syndrome: A placebo-controlled cross-over study on the effects of melatonin administered five hours before the individual dim light melatonin onset. J Sleep Res. June 1998; 7(2):135-43; Kayumov L, Brown G, Jindal R, Buttoo K, Shapiro C M. A randomized, double-blind, placebo-controlled crossover study of the effect of exogenous melatonin on delayed sleep phase syndrome. Psychosom Med. January-February 2001; 63(1):40-8; Buscemi N, Vandermeer B, Hooton N, Pandya R, Tjosvold L, Hartling L, Baker G, Klassen T P, Vohra S. The efficacy and safety of exogenous melatonin for primary sleep disorders. A meta-analysis. J Gen Intern Med. December 2005; 20(12): 1151-8), wherein it reduces the time it takes for an individual to fall asleep. Melatonin may also normalize the circadian rhythm and benefit shift workers and individuals with circadian rhythm disorders (Avery D, Lenz M, Landis C. Guidelines for prescribing melatonin. Ann Med. February 1998; 30(1):122-30; Kunz D, Mahlberg R, Muller C, Tilmann A, Bes F. Melatonin in patients with reduced REM sleep duration: two randomized controlled trials. J Clin Endocrinol Metab. January 2004; 89(1):128-34; Mundey K, Benloucif S, Harsanyi K, Dubocovich M L, Zee P C. Phase-dependent treatment of delayed sleep phase syndrome with melatonin. Sleep. Oct. 1, 2005; 28(10):1271-8).

Melatonin may also been shown to be effective in treating seasonal depression (Lewy A J, Bauer V K, Cutler N L, Sack R L. Melatonin treatment of winter depression: a pilot study. Psychiatry Res. Jan. 16, 1998; 77(1):57-61) and migraines (Peres M F, Zukerman E, da Cunha Tanuri F, Moreira F R, Cipolla-Neto J. Melatonin, 3 mg, is effective for migraine prevention. Neurology. Aug. 24, 2004; 63(4):757). Furthermore, blood pressure as well as stress hormones can be reduced by daily oral administration of melatonin in healthy men (Arangino S, Cagnacci A, Angiolucci M, Vacca A M, Longu G, Volpe A, Melis G B. Effects of melatonin on vascular reactivity, catecholamine levels, and blood pressure in healthy men. Am J Cardiol. May 1, 1999; 83(9):1417-9).

One aspect of the present invention includes the use of Melatonin for the regulation of sleep. U.S. Pat. Nos. 6,703, 412, 5,716,978, and 5,641,801 disclose methods of treating sleeplessness, sleep latency period, circadian rhythm disorders involving Melatonin.

For example, U.S. Pat. No. 6,703,412, entitled "Method of Treating Sleeplessness with Melatonin on an Acute Basis" purports to describe a method of treating sleeplessness in a human comprising the administration of an effective amount of not greater than 10 mg of melatonin or a pharmaceutically acceptable salt thereof. The method further comprises the administration of melatonin after a person has tried and failed to go to sleep, or has awakened from sleep and is unable to return to sleep. The method may be employed up to one hour from the person's desired waking time.

U.S. Pat. No. 5,716,978, entitled "Methods of Treating Circadian Rhythm Disorders" describes a method in which infants and blind humans employ the administration of Melatonin to produce a phase-shifting effect and reinstate a proper circadian rhythm. The method involves the administration of Melatonin from about 6 hours to about 19 hours prior to when a normal sleep phase should begin. The administration of Melatonin is to be less than 1 mg and at a time prior to a person's endogenous Melatonin onset time.

U.S. Pat. No. 5,641,801 entitled "Method of Reducing the Period before the Onset of Sleep" purports to describe a method of inducing sleep in an individual via the administration of a single dose of Melatonin comprising less than 1 mg to raise the peak plasma Melatonin levels to within physiological nocturnal levels of normal untreated individuals.

In an embodiment of the present invention, which is set forth in greater detail in Example 1 below, the supplemental composition may include Melatonin. A serving of the supplemental composition may include from about 0.001 g to about 0.01 g of Melatonin. The preferred dosage of a serving of the supplemental composition comprises about 0.0040 g of Melatonin.

Furthermore, in an embodiment of the present invention, which is set forth in greater detail in Example 1 below, the supplemental composition may include fine-milled Melatonin. A serving of the supplemental composition may include from about 0.0001 g to about 0.01 g of fine-milled Melatonin. The preferred dosage of a serving of the supplemental composition comprises about 0.0010 g of fine-milled Melatonin.

CoQ10

Coenzyme Q10 (CoQ10, ubiquinone) is found in the mitochondria of all cells and is involved in energy production. It is found at its highest concentrations in the heart, liver, kidney and pancreas. CoQ10 is a potent antioxidant in human blood (Weber C, Sejersgard Jakobsen T, Mortensen S A, Paulsen G, Holmer G. Antioxidative effect of dietary coenzyme Q10 in human blood plasma. Int J Vitam Nutr Res. 1994; 64(4):311-5) where it also acts to preserve vitamin E, another major antioxidant (Thomas S R, Neuzil J, Stocker R. Inhibition of LDL oxidation by ubiquinol-10. A protective mechanism for coenzyme Q in atherogenesis? Mol Aspects Med. 1997; 18 Suppl:S85-103).

Due to its high concentrations in the heart, CoQ10 is believed to benefit and strengthen the heart. Many heart-related diseases are thought to result from defective myocardial energy production and numerous studies have suggested that supplementation with CoQ10 is beneficial (Mortensen S A. Perspectives on therapy of cardiovascular diseases with coenzyme Q10 (ubiquinone). Clin Investig. 1993; 71(8 Suppl):S116-23). A meta-analysis of eight clinical trials supports the efficacy of CoQ10 for the treatment of congestive heart failure (Soja A M, Mortensen S A. Treatment of congestive heart failure with coenzyme Q10 illuminated by meta-analyses of clinical trials. Mol Aspects Med. 1997; 18 Suppl: S159-68). Another study has shown that individuals suffering from angina were able to exercise for longer periods when receiving CoQ10 (Kamikawa T, Kobayashi A, Yamashita T, Hayashi H, Yamazaki N. Effects of coenzyme Q10 on exercise tolerance in chronic stable angina pectoris. Am J Cardiol. Aug. 1, 1985; 56(4):247-51) as compared to untreated groups. Moreover, myocardial function was improved by CoQ10 in patients with disease conditions known to involve energy production deficits (Folkers K, Wolaniuk J, Simonsen R, Morishita M, Vadhanavikit S. Biochemical rationale and the cardiac response of patients with muscle disease to therapy with coenzyme Q10. Proc Natl Acad Sci USA. July 1985; 82(13):4513-6) wherein these patients also reported a 'subjective' improved sense of well-being. CoQ10 supplemented with iron and vitamin B6 has also appeared to prevent the progression of Alzheimer's disease, a neurological disease often associated with impaired mitochondrial function (Imagawa M, Naruse S, Tsuji S, Fujioka A, Yamaguchi H. Coenzyme Q10, iron, and vitamin B6 in genetically-confirmed Alzheimer's disease. Lancet. Sep. 12, 1992; 340(8820):671). Moreover, in another neurological disorder, CoQ10 in a phase II clinical trial was reported to slow the progression of Parkinson's disease (Shults C W, Oakes D, Kieburtz K, Beal M F, Haas R, Plumb S, Juncos J L, Nutt J, Shoulson I, Carter J, Kompoliti K, Perlmutter J S, Reich S, Stern M, Watts R L, Kurlan R, Molho E, Harrison M, Lew M; Parkinson Study Group. Effects of coenzyme Q10 in early Parkinson disease: evidence of slowing of the functional decline. Arch Neurol. October 2002; 59(10):1541-50) which often results in disturbed sleep and has been shown to involve impaired mitochondrial function and low levels of CoQ10 (Shults C W, Haas R H, Passov D, Beal M F. Coenzyme Q10 levels correlate with the activities of complexes I and II/III in mitochondria from parkinsonian and nonparkinsonian subjects. Ann Neurol. August 1997; 42(2):261-4).

Furthermore, CoQ10 has been successfully used to treat high blood pressure, eliminating the need for medication in many cases (Langsjoen P, Langsjoen P, Willis R, Folkers K. Treatment of essential hypertension with coenzyme Q10. Mol Aspects Med. 1994; 15 Suppl:S265-72). Migraines have also been successfully and safely treated with CoQ10 (Sandor P S, Di Clemente L, Coppola G, Saenger U, Fumal A, Magis D, Seidel L, Agosti R M, Schoenen J. Efficacy of coenzyme Q10 in migraine prophylaxis: a randomized controlled trial. Neurology. Feb. 22, 2005; 64(4):713-5) most likely due its effects on blood pressure.

In a Japanese study, CoQ10 was shown to provide relieve from snoring in about half of the subjects, displaying a decrease in the sound level of their snoring (Takasaki Y, Yoshida H, Kaneko Y, Kaneda R, Kurosaki S, Yamadera Y., An Analysis of Effectiveness of Activated Co-enzyme Q10 on Subjects by Using Acoustic Technology. Biopharma Ltd. Tokyo Japan). Specifically, about 44% of subjects displayed a decrease in the sound level of their snoring during the REM stage of sleep, about 40% of subjects showed a decrease in the sound level of their snoring during non-REM sleep stages I/II, and about 33% of subjects showed a decrease in the sound level of their snoring during non-REM sleep stages III/IV. Furthermore, subjects reported in questionnaires that their feeling of restfulness was improved upon waking.

In an embodiment of the present invention, which is set forth in greater detail in Example 1 below, the supplemental composition may include CoEnzyme Q10. A serving of the supplemental composition may include from about 0.0005 g to about 0.1000 g of CoEnzyme Q10. The preferred dosage of a serving of the supplemental composition comprises about 0.0010 g of CoEnzyme Q10.

Lemon Balm Leaf Extract

The plant *Melissa officinalis*, commonly known as Lemon balm is a member of the mint family and is often referred to as 'the calming herb". Lemon balm extract has proven antioxidant activity which likely contributes to its beneficial effects (Hohmann J, Zupko I, Redei D, Csanyi M, Falkay G, Mathe I, Janicsak G. Protective effects of the aerial parts of *Salvia officinalis, Melissa Officinalis* and *Lavandula angustifolia* and their constituents against enzyme-dependent and enzyme-independent lipid peroxidation. Planta Med. August 1999; 65(6):576-8). However, in the central nervous system, it possesses acetylcholine receptor activity (Wake G, Court J, Pickering A, Lewis R, Wilkins R, Perry E. acetylcholine receptor activity in European medicinal plants traditionally used to improve failing memory. J Ethnopharmacol. February 2000; 69(2):105-14), therefore suggesting that it may have another possible mechanism of action relating to cell-signaling.

Randomized, placebo-controlled, double-blind clinical studies investigating the acute effects of Lemon balm extract on cognition and mood have demonstrated a calming effect (Kennedy D O, Scholey A B, Tildesley N T, Perry E K, Wesnes K A. Modulation of mood and cognitive performance following acute administration of *Melissa officinalis* (lemon balm). Pharmacol Biochem Behav. July 2002; 72(4):953-64) in addition to the effect of improved mood (Kennedy D O, Wake G, Savelev S, Tildesley N T, Perry E K, Wesnes K A, Scholey A B. Modulation of mood and cognitive performance following acute administration of single doses of *Melissa officinalis* (Lemon balm) with human CNS nicotinic and muscarinic receptor-binding properties. Neuropsychopharmacology. October 2003; 28(10):1871-81). Lemon balm extract has also shown potential in reducing the negative mood effects of stress in clinical trials (Kennedy D O, Little W, Scholey A B. Attenuation of laboratory-induced stress in humans after acute administration of *Melissa officinalis* (Lemon Balm). Psychosom Med. July-August 2004; 66(4):607-13).

Moreover, the cognitive function of Alzheimer's patients has been shown to be improved by the use Lemon balm extract (Akhondzadeh S, Noroozian M, Mohammadi M, Ohadinia S, Jamshidi A H, Khani M. *Melissa officinalis* extract in the treatment of patients with mild to moderate Alzheimer's disease: a double blind, randomised, placebo controlled trial. J Neurol Neurosurg Psychiatry. July 2003; 74(7):863-6). In this study, the treatment group also displayed less agitation than the placebo group, suggesting an improvement in mood. Furthermore, clinical trials have demonstrated that Lemon balm can be effective at reducing stress and anxiety when used in combination with *Valeriana* (Kennedy D O, Little W, Haskell C F, Scholey A B. Anxiolytic effects of a combination of *Melissa officinalis* and *Valeriana officinalis* during laboratory induced stress. Phytother Res. February 2006; 20(2):96-102). Another study has shown that when presented in a lozenge also containing Lavender oil and hops, Lemon balm can alter brain-waves related to working memory, leading to the induction of a state of relaxation and an improved ability to cope with emotional and physiological stress (Dimpfel W, Pischel I, Lehnfeld R. Effects of lozenge containing lavender oil, extracts from hops, lemon balm and oat on electrical brain activity of volunteers. Eur J Med Res. Sep. 29, 2004; 9(9):423-31).

In an embodiment of the present invention, which is set forth in greater detail in Example 1 below, the supplemental composition may include Lemon Balm leaf extract. A serving of the supplemental composition may include from about 0.0010 g to about 0.1000 g of Lemon Balm leaf extract. The preferred dosage of a serving of the supplemental composition comprises about 0.0800 g of Lemon Balm leaf extract.

Hops Cone Extract (*Humulus lupulus*)

The hop plant (*Humulus lupulus*) is a flowering vine used traditionally as a sedative to assist with anxiety reduction and sleep difficulties. In mice, hops extract displays sleep-enhancing and antidepressant activities (Zanoli P, Rivasi M, Zavatti M, Brusiani F, Baraldi M. New insight in the neuropharmacological activity of *Humulus lupulus* L. J Ethnopharmacol. Oct. 31, 2005; 102(1):102-6).

In vitro tests have shown that hops contain compounds with antioxidant and chemoprotective activity as well as compounds that can induce detoxification enzymes (Dietz B M, Kang Y H, Liu G, Eggler A L, Yao P, Chadwick L R, Pauli G F, Farnsworth N R, Mesecar A D, van Breemen R B, Bolton J L. Xanthohumol isolated from *Humulus lupulus* Inhibits menadione-induced DNA damage through induction of quinone reductase. Chem Res Toxicol. August 2005; 18(8):1296-305).

A combination of valerian and hops has been shown to interact with adenosine receptors (Muller C E, Schumacher B, Brattstrom A, Abourashed E A, Koetter U. Interactions of valerian extracts and a fixed valerian-hop extract combination with adenosine receptors. Life Sci. Sep. 6, 2002; 71(16):1939-49) to aid in the maintenance of sleep. Moreover, binding of the valerian-hop combination to melatonin and serotonin receptors has also been shown (Abourashed E A, Koetter U, Brattstrom A. In vitro binding experiments with a Valerian, hops and their fixed combination extract (Ze91019) to selected central nervous system receptors. Phytomedicine. November 2004; 11(7-8):633-8). These two receptor types are also known to be involved in the sleep process. Furthermore, hop extract has been shown to modulate the gamma-aminobutyric acid receptor (GABA(A) receptors) and display GABA-like activity (Aoshima H, Takeda K, Okita Y, Hossain S J, Koda H, Kiso Y. Effects of beer and hop on ionotropic gamma-aminobutyric acid receptors. J Agric Food Chem. Apr. 5, 2006; 54(7):2514-9) relating to sleep. GABA is an inhibitory neurotransmitter that can induce relaxation and sleep. Modulation of any or all of these receptors may mediate the sleep-inducing activity of hops.

Most of the studies examining the efficacy of hops to aid sleep employ hops in combination with other compounds acting on various receptors known to be involved in sleep regulation. A combination of valerian and hops has been shown to reduce the time taken to fall asleep and results in a more refreshed feeling in the morning in subjects suffering from mild to moderate insomnia (Fussel A, Wolf A, Brattstrom A. Effect of a fixed valerian-Hop extract combination (Ze 91019) on sleep polygraphy in patients with non-organic insomnia: a pilot study. Eur J Med Res. Sep. 18, 2000; 5(9):385-90).

In an embodiment of the present invention, which is set forth in greater detail in Example 1 below, the supplemental composition may include Hops cone extract. A serving of the supplemental composition may include from about 0.0010 g to about 0.1000 g of Hops cone extract. The preferred dosage of a serving of the supplemental composition comprises about 0.0200 g of Hops cone extract.

Lavender Flower (*Lavandula officinalis*)

Oil from *Lavandula officinalis*, commonly known as the Lavender plant is frequently used in aromatherapy as a mode to induce relaxation. The mild sedative effects of Lavender have been demonstrated in animals and humans (Lis-Balchin M, Hart S. Studies on the mode of action of the essential oil of lavender (*Lavandula angustifolia* P. Miller). Phytother Res. September 1999; 13(6):540-2). Further to the sedative effect, Lavender oil has been shown to reduce agitation of patients suffering from dementia (Holmes C, Hopkins V, Hensford C, MacLaughlin V, Wilkinson D, Rosenvinge H. Lavender oil as a treatment for agitated behaviour in severe dementia: a placebo controlled study. Int J Geriatr Psychiatry. April 2002; 17(4):305-8). Moreover, Lavender has also been shown be beneficial for treating depression (Akhondzadeh S, Kashani L, Fotouhi A, Jarvandi S, Mobaseri M, Moin M, Khani M, Jamshidi A H, Baghalian K, Taghizadeh M. Comparison of *Lavandula angustifolia* Mill. tincture and imipramine in the treatment of mild to moderate depression: a double-blind, randomized trial. Prog Neuropsychopharmacol Biol Psychiatry. February 2003; 27(1):123-7). Additionally, the sleep-inducing effects of other compounds may be increased by Lavender (Gyllenhaal C, Merritt S L, Peterson S D, Block K I, Gochenour T. Efficacy and safety of herbal stimulants and sedatives in sleep disorders. Sleep Med Rev. June 2000; 4(3): 229-251).

U.S. Pat. No. 5,958,462, entitled "Therapeutic Bath Salts and Method of Use," describes a composition comprising magnesium, carbonate and copper compounds and optionally essential oils including that of Lavender. The composition comprises bath salts purported to be helpful in the relaxation of muscles, elimination or reduction of muscle spasms, and the overall enhancement of a person's mood when used as an aromatherapy.

In an embodiment of the present invention, which is set forth in greater detail in Example 1 below, the supplemental composition may include Lavender Flower powder. A serving of the supplemental composition may include from about 0.0010 g to about 0.0100 g of Lavender Flower powder. The preferred dosage of a serving of the supplemental composition comprises about 0.0050 g of Lavender Flower powder.

Passion Flower Extract

Passion flower has been used traditionally for relaxation and as a sleep-aid as well as a treatment for anxiety. The main active component of Passionflower is thought to by chrysin, one of several flavonoids which have been isolated from this plant (Menghini A, Mancini L A. TLC determination of flavonoid accumulation in clonal populations of *Passiflora incarnata* L. Pharmacol Res Commun. December 1988; 20 Suppl 5:113-6; Pereira C A, Yariwake J H, Lancas F M, Wauters J N, Tits M, Angenot L. A HPTLC densitometric determination of flavonoids from *Passiflora alata, P. edulis, P. incarnata* and *P. caerulea* and comparison with HPLC method. Phytochem Anal. July-August 2004; 15(4):241-8). In mice, chrysin has been shown to act as an agonist of benzodiazepine receptors and also possess anti-anxiety activity (Wolfman C, Viola H, Paladini A, Dajas F, Medina J H. Possible anxiolytic effects of chrysin, a central benzodiazepine receptor ligand isolated from *Passiflora coerulea*. Pharmacol Biochem Behav. January 1994; 47(1):1-4). Studies have shown that, in mice, Passionflower extract reduces anxiety and induces sleep (Soulimani R, Younos C, Jarmouni S, Bousta D, Misslin R, Mortier F. Behavioural effects of *Passiflora incarnata* L. and its indole alkaloid and flavonoid derivatives and maltol in the mouse. J Ethnopharmacol. June 1997; 57(1):11-20). Clinical trials in humans have further demonstrated that Passionflower is effective in the treatment of anxiety (Akhondzadeh S, Naghavi H R, Vazirian M, Shayeganpour A, Rashidi H, Khani M. Passionflower in the treatment of generalized anxiety: a pilot double-blind randomized controlled trial with oxazepam. J Clin Pharm Ther. October 2001; 26(5):363-7).

One aspect of the present invention includes the use of Passionflower extract for the reduction of stress and anxiety. U.S. Pat. Nos. 6,080,410 and 5,681,578 describe a method and composition, respectively, employing Passionflower extracts for the reduction of stress and anxiety.

U.S. Pat. No. 6,080,410, entitled "Method for Reducing Daily Stress and Anxiety in Adults," describes a method of employing a novel dietary supplement which serves a general relaxant comprised of Kava root extract, and at least one of Passionflower, Chamomile Flower, Hops, and Schizandra Fruit. The method claims to reduce daily stress and anxiety in adults. It is administered in capsule format.

U.S. Pat. No. 5,681,578, entitled "Composition for Relieving Stress Anxiety, Grief, And Depression," describes a composition comprising gamma Aminobutyric acid, glutamine, glycine, magnesium, passionflower, primal officinalis and vitamin B6. The composition is purported to relieve stress, anxiety, grief and depression.

In an embodiment of the present invention, which is set forth in greater detail in Example 1 below, the supplemental composition may include Passionflower extract. A serving of the supplemental composition may include from about 0.0010 g to about 0.0100 g of Passionflower extract. The preferred dosage of a serving of the supplemental composition comprises about 0.0020 g of Passionflower extract.

Skullcap (*Scutellaria lateriflora*)

*Scutellaria*, also known commonly as Skullcap, is a member of the mint family and has been used traditionally to treat depression and stress. Studies in mice indicate that Skullcap reduces anxiety (Awad R, Arnason J T, Trudeau V, Bergeron C, Budzinski J W, Foster B C, Merali Z. Phytochemical and biological analysis of skullcap (*Scutellaria lateriflora* L.): a medicinal plant with anxiolytic properties. Phytomedicine. November 2003; 10(8):640-9). The effects of Skullcap may be at least partially mediated by antagonism of serotonin receptors (Gafner S, Bergeron C, Batcha L L, Reich J, Arnason J T, Burdette J E, Pezzuto J M, Angerhofer C K. Inhibition of [3H]-LSD binding to 5-HT7 receptors by flavonoids from *Scutellaria lateriflora*. J Nat Prod. April 2003; 66(4):535-7). A clinical study involving healthy volunteers also demonstrated that Skullcap reduces anxiety (Wolfson P, Hoffmann D L. An investigation into the efficacy of *Scutellaria lateriflora* in healthy volunteers. Altern Ther Health Med. March-April 2003; 9(2):74-8).

U.S. Pat. No. 7,045,158, entitled "Standardized Extracts of *Scutellaria Laterifloa*," describes an improved extract of *Scutellaria Laterifloa* and relates to a pharmaceutical composition prepared from said extract wherein it is suitable for treating anxiety, insomnia, convulsions, muscle tension and spasms.

In an embodiment of the present invention, which is set forth in greater detail in Example 1 below, the supplemental composition may include Skullcap powder. A serving of the supplemental composition may include from about 0.0001 g to about 0.0100 g of Skullcap powder. The preferred dosage of a serving of the supplemental composition comprises about 0.0010 g of Skullcap powder.

Valerian Root (*Valeriana officinalis*)

*Valeriana officinalis*, wherein the root, normally called Valerian root, is a perennial herb traditionally used as a sedative and sleep-aid. Compounds from Valerian interact with GABA, melatonin, and/or adenosine systems through binding to certain melatonin and serotonin receptor subtypes (Abourashed E A, Koetter U, Brattstrom A. In vitro binding experiments with a Valerian, hops and their fixed combination extract (Ze91019) to selected central nervous system receptors. Phytomedicine. November 2004; 11(7-8):633-8), particularly the $5\text{-HT}_{5A}$ subtype (Dietz B M, Mahady G B, Pauli G F, Farnsworth N R. Valerian extract and valerenic acid are partial agonists of the 5-HT5a receptor in vitro. Brain Res Mol Brain Res. Aug. 18, 2005; 138(2):191-7). Interaction with this receptor is thought to be responsible for the sleep-inducing and maintenance effect of Valerian root extract.

Valerian root extract has proven to be useful in several clinical trials. Subjective self-evaluation of sleep quality improved in a valerian supplemented group as part of a randomized controlled trial (Leathwood P D, Chauffard F, Heck E, Munoz-Box R. Aqueous extract of valerian root (*Valeriana officinalis* L.) improves sleep quality in man. Pharmacol Biochem Behav. July 1982; 17(1):65-71), compared to control groups. In another clinical trial, the valerian group reported improved sleep over the placebo group, with 89% of participants reporting improved sleep (Lindahl O, Lindwall L. Double blind study of a valerian preparation. Pharmacol Biochem Behav. April 1989; 32(4):1065-6). Sleep was additionally improved in children with various intellectual deficits, particularly those with hyperactivity (Francis A J, Dempster R J. Effect of valerian, *Valeriana edulis*, on sleep difficulties in children with intellectual deficits: randomised trial. Phytomedicine. May 2002; 9(4):273-9).

One aspect of the present invention includes the use of Valerian for improving the quality of sleep and reducing minor aches and pains. U.S. Pat. Nos. 6,869,622 and 6,383,527 describe respective compositions for improving the quality of sleep and alleviating muscular aches and strains, particularly with respect to those in the lower back.

For example, U.S. Pat. No. 6,869,622, entitled "Composition for Improving Sleep Quality and Efficiency, And Method of Preparing and Using the Composition," describes a pharmaceutically active extract of the plant root family of Valerianaceae and its usefulness in improving sleep quality and efficiency. The patent purports to relate to a method for reducing the number of times a patient wakes after sleep onset, comprising administering to the patient a pharmaceutically-active extract of the root of a plant of the family Valerianaceae, wherein it is processed via an ethanolic and water extraction. Furthermore, a single dosage is administered between the range of 50 mg and 5000 mg approximately one-half and two hours prior to bedtime.

U.S. Pat. No. 6,383,527, entitled "Compositions Comprising Valerian Extracts, Isovaleric Acid or Derivatives Thereof with a NSAID," purports to describe a combination of valerian extract or isovaleric acid or a derivative in with a nonsteroidal anti-inflammatory compound for treating acute muscular aches, strains and sprains, and in particular lower back pain.

In an embodiment of the present invention, which is set forth in greater detail in Example 1 below, the supplemental composition may include Valerian Root. A serving of the supplemental composition may include from about 0.1000 g to about 1.000 g of Valerian Root. The preferred dosage of a serving of the supplemental composition comprises about 0.1200 g of Valerian Root.

Willow Bark Extract (Providing Salicin) (*Salix alba*) 25% Salicin

Willow bark (*Salix alba*) is a source of salicin, a precursor of acetylsalicylic acid (aspirin) traditionally used to treat pain, fever and inflammation. In a blind clinical trial, willow bark was demonstrated to be effective at relieving back pain (Chrubasik S, Eisenberg E, Balan E, Weinberger T, Luzzati R, Conradt C. Treatment of low back pain exacerbations with willow bark extract: a randomized double-blind study. Am J Med. July 2000; 109(1):9-14). After four weeks, 39% of the high salicin group (n=65) were pain-free, 21% of the low salicin group (n=67) were pain-free, and only 6% of the placebo group (n=59) were pain-free. Willow bark extract has also been shown to effectively reduce arthritis pain (Schmid B, Ludtke R, Selbmann H K, Kotter I, Tschirdewahn B, Schaffner W, Heide L. Efficacy and tolerability of a standardized willow bark extract in patients with osteoarthritis: randomized placebo-controlled, double blind clinical trial. Phytother Res. June 2001; 15(4):344-50).

The diminishment of bodily pain is an integral part of quality sleep. The inclusion of Willow Back Extract aids in the alleviation of minor bodily pains, leading to an improvement in sleep quality and a reduction in sleep disruption due to discomfort.

One aspect of the present invention includes the use of Willow bark for the attenuation of minor aches and pains, leading to an improved quality of sleep. U.S. Pat. Nos. 6,770,263 and 6,312,736 describe compositions for the treatment, e.g., alleviation, of aches and pains.

For example, U.S. Pat. No. 6,770,263, entitled "Compositions and Methods for the Treatment of Aches and Pains," purports to describe methods and compositions useful for treating aches and/or pains. The composition comprises an aqueous medium having dispersed or dissolved therein an analgesic selected from the group consisting of white willow bark, aspirin, ibuprofen, naproxen, and any combination thereof. The composition is then administered in an effective amount across a mucosal membrane.

U.S. Pat. No. 6,312,736, entitled "Herbal Composition to Relieve Pain," describes a composition used to relieve pain and other symptoms associated with migraines and other types of headaches. The composition comprises a combination of White Willow bark extract, Kava Kava root extract, Feverfew extract, Ginger root extract, Guarana extract, and Vitamin B6 wherein the composition may be combined with liposomes to carry the composition in a sublingual dosage for fast pain relief.

In an embodiment of the present invention, which is set forth in greater detail in Example 1 below, the supplemental composition may include Willow bark extract. A serving of the supplemental composition may include from about 0.1000 g to about 1.000 g of Willow bark extract. The preferred dosage of a serving of the supplemental composition comprises about 0.1500 g Willow bark extract.

The present invention, according to an embodiment thereof, provides a method which includes the step of consuming a composition, wherein the method may, for example, alleviate minor aches and pains, speedily induce sleep, as well as provide for maintenance of sleep thereby promoting a good quality, restful sleep. In an embodiment of the present invention, the method includes the daily consumption, prior to going to sleep with the intent of a full night's sleep, of a sleep-promoting and pain-relief composition that may include at least an extract of Valerian Root, an extract of Willow Bark and Melatonin or a derivative thereof. Furthermore, the sleep-promoting and pain-relief composition may further comprise Coenzyme Q10, Lemon Balm leaf extract, Hops cone extract, Lavender flower extract, Passionflower extract, and Skullcap powder.

The present supplemental composition, or those similarly envisioned by one of skill in the art, may be utilized in methods to alleviate minor aches and pains, speedily induce sleep, as well as provide for maintenance of sleep thereby promoting a good quality, restful sleep in a formulation designed to be consumed on a daily basis prior to going to sleep with the intent of a night's rest.

In an embodiment of the present invention, the composition may include a time-release mechanism, e.g., wherein the time-release mechanism provides 4 hours of active compound release. Also, in various embodiments, the melatonin may be incorporated into a tablet coating to promote sleep more quickly, e.g., to promote instant or immediate sleep.

Although the following example illustrates the practice of the present invention one of its embodiments the example should not be interpreted as limiting the scope of the invention. Other embodiments of the present invention will be apparent to those of skill in the art form consideration of the specification and example.

Example 1

A supplemental composition is provided on a daily basis, prior to going to sleep with the intent on a full night's rest, the composition utilizing a dual-release caplet formulation comprising Melatonin (0.0040 g), fine-milled Melatonin (0.0010 g), Coenzyme Q10 (0.0010 g), Hops cone extract (0.0200 g), Lavender flower powder (0.0050 g), Passionflower extract (0.0020 g), Skullcap powder (0.0010 g), Lemon Balm leaf extract (0.0800 g), deodorized Valerian root (0.1200 g) and Willow bark extract (0.1500 g).

Directions: As a supplemental composition, 1 caplet is orally administered with an 8 oz. glass of water once daily prior to going to sleep. Preferably, the supplemental composition is consumed with the intent of a full night's sleep.

What is claimed:

1. A composition for promoting sleep in a human or animal comprising:
    about 0.1200 g of an extract of Valerian Root per serving;
    about 0.1500 g of an extract of Willow Bark per serving;
    about 0.0040 g of Melatonin per serving;
    about 0.0010 g of fine-milled Melatonin per serving;
    about 0.0200 g of an extract of Hops cone per serving;
    about 0.0050 g of Lavender flower powder per serving;
    about 0.0020 g of an extract of Passionflower per serving;
    about 0.0010 g of Skullcap powder per serving;
    about 0.0010 g of Coenzyme Q10 per serving; and
    about 0.0800 g of an extract of Lemon Balm per serving.

2. The composition of claim 1, wherein the composition further comprises a time-release mechanism.

3. The composition of claim 1, wherein the composition is provided in a tablet form.

4. The composition of claim 3, wherein the Melatonin or fine-milled Melatonin is incorporated into a coating of the tablet.

5. A composition for promoting sleep in a human or animal comprising:
    an extract of Valerian Root;
    an extract of Willow Bark;
    Melatonin;
    fine-milled Melatonin;
    an extract of Hops cone;
    Lavender flower powder;
    an extract of Passionflower;
    Skullcap powder;
    Coenzyme Q10; and
    an extract of Lemon Balm.

6. The composition of claim 5, wherein the composition further comprises a time-release mechanism.

7. The composition of claim 5, wherein the composition is provided in a tablet form.

8. The composition of claim 7, wherein the Melatonin or fine-milled Melatonin is incorporated into a coating of the tablet.

* * * * *